United States Patent
Bellows et al.

(10) Patent No.: US 11,793,593 B2
(45) Date of Patent: *Oct. 24, 2023

(54) LIGHTING ASSEMBLIES FOR MEDICAL DEVICE SUSPENSION SYSTEM

(71) Applicant: American Sterilizer Company, Mentor, OH (US)

(72) Inventors: Lance Clark Bellows, Painesville, OH (US); Bernard John Moss, Perry, OH (US); Michael Hollopeter, Kirtland, OH (US); Joseph James Groszek, Lakewood, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/601,284

(22) PCT Filed: Apr. 1, 2020

(86) PCT No.: PCT/US2020/026271
§ 371 (c)(1),
(2) Date: Oct. 4, 2021

(87) PCT Pub. No.: WO2020/206043
PCT Pub. Date: Oct. 8, 2020

(65) Prior Publication Data
US 2022/0168064 A1    Jun. 2, 2022

Related U.S. Application Data

(60) Provisional application No. 62/828,090, filed on Apr. 2, 2019.

(51) Int. Cl.
*A61B 90/35* (2016.01)
*F21V 21/36* (2006.01)
(Continued)

(52) U.S. Cl.
CPC .......... *A61B 90/35* (2016.02); *F21V 21/088* (2013.01); *F21V 21/36* (2013.01);
(Continued)

(58) Field of Classification Search
CPC .... F21V 21/044; F21V 21/049; F21V 21/025; F21Y 2107/70; F21Y 2103/30; F21Y 2103/33; A61B 90/35
See application file for complete search history.

(56) References Cited

U.S. PATENT DOCUMENTS 2,173,325 A    9/1939  Alexander
5,337,225 A    8/1994  Brookman
(Continued)

FOREIGN PATENT DOCUMENTS

CN    2917368 Y    7/2007
CN    101825227 A    9/2010
(Continued)

OTHER PUBLICATIONS

PCT International Search Report and Written Opinion of the International Searching Authority for related International Application No. PCT/US2020/026271 dated Dec. 16, 2020.
(Continued)

*Primary Examiner* — Julie A Bannan
(74) *Attorney, Agent, or Firm* — Renner, Otto, Boisselle & Sklar, LLP

(57) ABSTRACT

Embodiments include a lighting assembly includes an elongate gasket body formed of a resilient, optically transmissive material. The gasket body includes a light source cavity at least partially defined by a light transmission portion and an attachment channel configured to attach the gasket body to a mount. A light source is disposed in the light source cavity. Other embodiments include securement ring including a clamp portion and a lighting assembly portion. The clamp
(Continued)

portion includes first and second segments, each being semiannular in shape and curving between first and second ends, the first end of the first segment coupled to the second end of the second segment and the second end of the first segment coupled to the first end of the second segment to collectively form an aperture. The lighting assembly portion includes a first and second segments, each being semiannular in shape and including a light source.

19 Claims, 13 Drawing Sheets

(51) Int. Cl.
    *F21V 21/088* (2006.01)
    *F21V 33/00* (2006.01)
    *F21W 131/20* (2006.01)
    *F21W 131/205* (2006.01)

(52) U.S. Cl.
    CPC ..... *F21V 33/0068* (2013.01); *F21W 2131/20* (2013.01); *F21W 2131/205* (2013.01)

(56) References Cited

U.S. PATENT DOCUMENTS

| | | | |
|---|---|---|---|
| 5,848,837 A | 12/1998 | Gustafson | |
| 6,471,381 B2 | 10/2002 | Atkinson | |
| 6,866,410 B2 | 3/2005 | Jesurun et al. | |
| 7,082,721 B2 | 8/2006 | Whitehead | |
| 7,144,139 B2 | 12/2006 | Kramer et al. | |
| 9,328,904 B2 | 5/2016 | Volkenand et al. | |
| 9,469,244 B2 | 10/2016 | Salter et al. | |
| 9,587,800 B2 | 3/2017 | Salter et al. | |
| 9,687,305 B2 | 6/2017 | Weller | |
| 10,041,625 B2 | 8/2018 | Volkenand et al. | |
| 10,966,796 B2 | 4/2021 | Bellows et al. | |
| 2003/0161152 A1 | 8/2003 | Jesurun et al. | |
| 2005/0231947 A1* | 10/2005 | Sloan | G09F 9/33 362/235 |
| 2005/0242261 A1 | 11/2005 | Brahler et al. | |
| 2006/0112482 A1 | 6/2006 | Walker et al. | |
| 2009/0196020 A1 | 8/2009 | Tsai | |
| 2011/0260598 A1 | 10/2011 | Liu | |
| 2015/0036375 A1 | 2/2015 | Gold | |
| 2016/0025315 A1 | 1/2016 | Igaki et al. | |
| 2016/0131345 A1 | 5/2016 | Ammer | |
| 2016/0296297 A1 | 10/2016 | Perplies et al. | |
| 2019/0072260 A1 | 3/2019 | Nichols et al. | |

FOREIGN PATENT DOCUMENTS

| | | |
|---|---|---|
| DE | 102015112041 A1 | 1/2017 |
| DE | 102016219904 A1 | 4/2018 |
| FR | 2886238 A1 | 12/2006 |
| KR | 20150004549 A | 1/2015 |
| WO | 2008134424 A2 | 11/2008 |
| WO | 2018069489 A1 | 4/2018 |

OTHER PUBLICATIONS

International Preliminary Report on Patentability for related International Application No. PCT/US2020/026271 dated Oct. 14, 2021.

* cited by examiner

LIGHTING ASSEMBLIES FOR MEDICAL DEVICE SUSPENSION SYSTEM This application is a national phase of International Application No. PCT/US2020/026271 filed 1 Apr. 2020, which claims priority to U.S. Application No. 62/828,090 filed 2 Apr. 2019, the entire disclosures of which are hereby incorporated by reference.

FIELD OF INVENTION

This application relates generally to a medical device suspension system for use in, for example, a hospital examination room, a clinic, a surgery room or an emergency room; and more particularly to lighting assemblies for a medical device suspension system.

BACKGROUND

Medical device suspension systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others.

In these health treatment settings there is often a need for low level lighting that may provide a low level of illumination for a purpose such as ambient lighting, endo procedures, task lighting, accent lighting, and the like. Conventional lighting assemblies providing this functionality are typically provided as separate, additional components that can be difficult to assemble and/or attach to the medical device suspension system, and can detract from the aesthetics and/or functionality of the medical device suspension system.

SUMMARY OF INVENTION

The application relates to a medical device suspension system and to lighting assemblies for a medical device suspension system. The lighting assemblies of the present disclosure may provide low level of illumination for purposes such as ambient lighting, endo procedures, task lighting, accent lighting, and the like, and may also provide added functionality that allows the lighting assembly to replace one or more components utilized with a conventional medical device suspension system. In many instances, the lighting assemblies of the present disclosure may be retrofitted to existing conventional medical device suspension systems by substituting the lighting assembly with an existing component (e.g., a gasket and/or securement ring).

In accordance with one aspect of the present disclosure, a lighting assembly includes: an elongate gasket body extending along a length and formed of a resilient, optically transmissive material, the gasket body including: a light source cavity extending along the length, the light source cavity at least partially defined by a light transmission portion, the light source cavity being enclosed as viewed in a plane transverse to the length; and an attachment channel extending along the length, the attachment channel configured to attach the gasket body to a mount; and a light source disposed in the light source cavity and extending along the length, the light source arranged such that light emitted from the light source is incident and transmitted through the light transmission portion of the gasket body.

In some embodiments, the gasket body further includes a sealing protrusion extending along the length, the sealing protrusion including a cavity extending along the length and being at least partially defined by a convex contact portion as viewed in a plane transverse to the length.

In some embodiments, the gasket body further includes an attachment channel extending along the length, the additional attachment channel configured to attach the gasket body to an additional mount.

In some embodiments, the gasket body extends along the length between a first end and a second end, the light source cavity being open at at least one of the first end and the second end.

In some embodiments, the length of the gasket extends along a perimeter of a predetermined shape.

In some embodiments, the material of the gasket body includes silicone, rubber, polycarbonate, thermoplastic polymer, thermoset polymer, plastic, or blends thereof. In some embodiments, the material diffuses light emitted from the light source and transmitted therethrough.

In some embodiments, the light source includes one or more solid-state light emitters.

In some embodiments, the one or more solid-state light emitters are mounted on a flexible substrate.

In some embodiments, the attachment channel includes protrusions configured to engage the mount upon insertion into the attachment channel.

In some embodiments, the protrusions include one or more of ribs, barbs, and bumps.

In some embodiments, the light transmission portion includes an inner surface facing a light emitting surface of the light source; and a distance from the light emitting surface of the light source to the inner surface along a direction orthogonal to the light emitting surface is 1 mm to 20 mm. In some embodiments, the distance from the light emitting surface of the light source to the inner surface along a direction orthogonal to the light emitting surface is 5 mm to 10 mm.

In some embodiments, a thickness of the light transmission portion along a direction orthogonal to the light emitting surface is 1 mm to 10 mm.

In some embodiments, a thickness of the light transmission portion along a direction orthogonal to the light emitting surface is 5 mm to 10 mm.

In some embodiments, a medical device suspension system includes: a mounting plate; a spindle attached to the mounting plate; a canopy including opposed major surfaces that are spaced apart from one another in a thickness direction, an end surface extending between the opposed major surfaces, and an orifice extending through the opposed major surfaces, the spindle extending through the orifice; and the lighting assembly in accordance with the present disclosure, wherein the end surface of the canopy is disposed in the attachment channel. In some embodiments, the spindle extends through a ceiling or wall structure and the canopy is positioned adjacent a surface of the ceiling or wall structure with the lighting assembly in contact with the surface. In some embodiments, a securement ring retains the canopy in place with respect to the spindle. In some embodiments, the securement ring includes an additional light source. In some embodiments, the spindle extends along a longitudinal axis, and the lighting assembly is configured to radially emit light about the longitudinal axis.

In accordance with another aspect of the present disclosure, a securement ring is mountable to a cylindrical support member, the securement ring having a height along a longitudinal axis and including: a clamp portion including a first segment and a second segment, each of the first and second segments of the clamp portion being semi-annular in shape and curving about the longitudinal axis between a first end and a second end, the first end of the first segment coupled to the second end of the second segment and the second end of the first segment coupled to the first end of the second segment such that the segments collectively form an aperture; and a lighting assembly portion including a first segment and a second segment, each of the first and second segments of the lighting assembly portion being semi-annular in shape and curving about the longitudinal axis between a first end and a second end, an outer surface of each segment of the lighting assembly portion including a recess in which a light source is disposed.

In some embodiments, the light source includes one or more solid-state light emitters.

In some embodiments, the one or more solid-state light emitters are arranged to radially emit light about the longitudinal axis.

In some embodiments, the one or more solid-state light emitters are mounted on a flexible substrate.

In some embodiments, the securement ring further including a lens cover at the outer surface that covers the light source. In some embodiments, the lens cover diffuses light emitted from the light source and transmitted therethrough.

In some embodiments, the segments of the lighting assembly portion are removably attached to respective segments of the clamp portion.

In some embodiments, a bottom surface of the first segment of the lighting assembly portion includes pins and a top surface of the first segment of the clamp portion includes holes that cooperate with the pins.

In some embodiments, a medical device suspension system includes: a mounting plate; a spindle attached to the mounting plate; a canopy including opposed major surfaces that are spaced apart from one another in a thickness direction, an end surface extending between the opposed major surfaces, and an orifice extending through the opposed major surfaces, the spindle extending through the orifice; and the securement ring of the present disclosure retaining the canopy in place with respect to the spindle. In some embodiments, the spindle extends through a ceiling or wall structure and the canopy is positioned adjacent a surface of the ceiling or wall structure. In some embodiments, the medical device suspension system further including a gasket at the end surface of the canopy. In some embodiments, the gasket includes an additional light source.

In some embodiments, a medical device suspension system includes: a mounting plate; a spindle attached to the mounting plate; a cable management cover disposed around a portion of the spindle; a canopy including opposed major surfaces that are spaced apart from one another in a thickness direction, an end surface extending between the opposed major surfaces, and an orifice extending through the opposed major surfaces, the spindle extending through the orifice; and the securement ring of any one of claims 21-28 retaining the canopy in place with respect to the cable management cover. In some embodiments, the spindle extends through a ceiling or wall structure and the canopy is positioned adjacent a surface of the ceiling or wall structure. In some embodiments, the medical device suspension system further including a gasket at the end surface of the canopy. In some embodiments, the gasket includes an additional light source.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the present disclosure.

DETAILED DESCRIPTION

Figure 1:
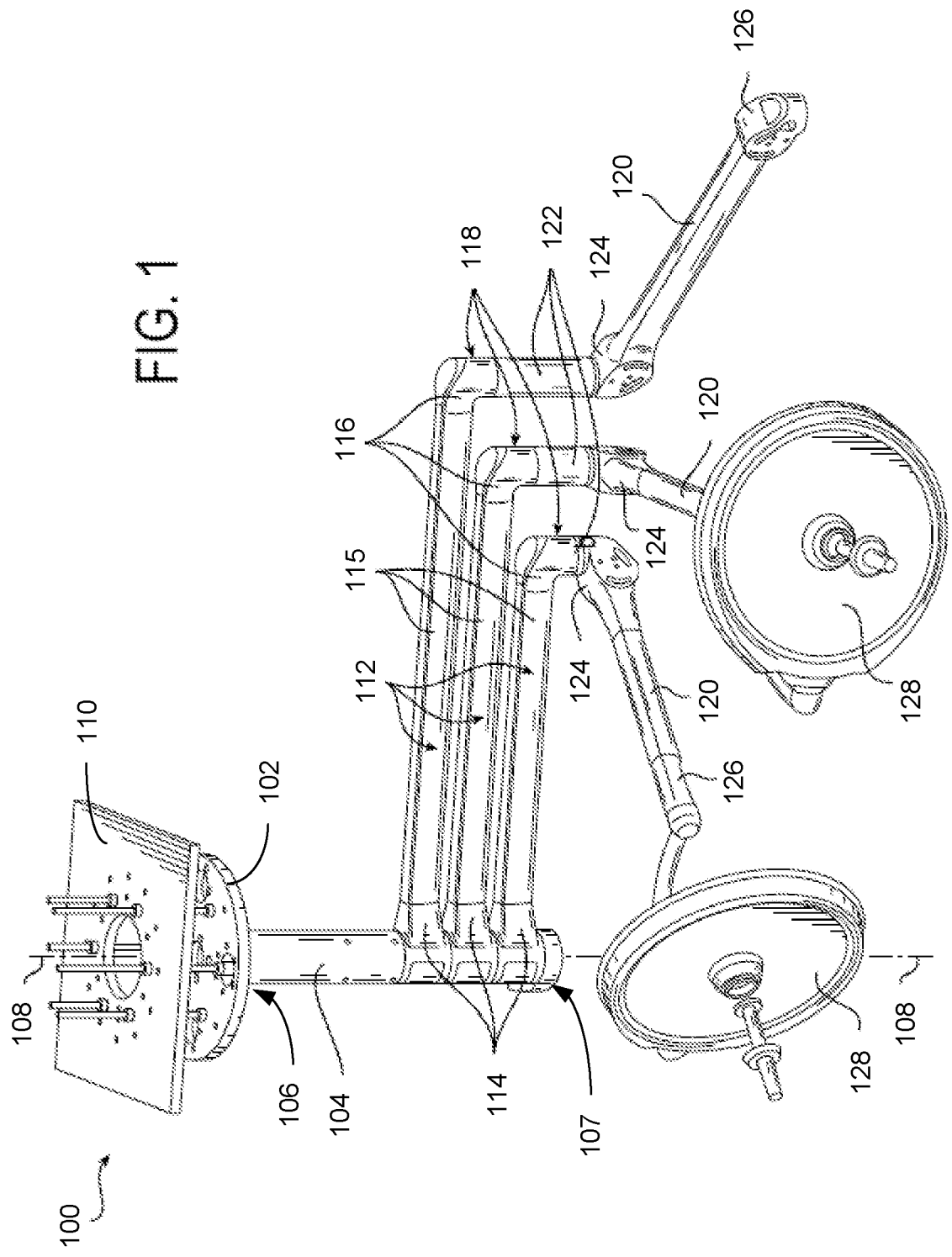
FIG. 1 is a schematic perspective view of parts of an exemplary medical device suspension system in accordance with an embodiment of the present disclosure.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

With initial reference to FIG. 1, parts of an exemplary medical device suspension system are shown at 100. The medical device suspension system 100 includes a primary (e.g., central) spindle 104 that is suspended from a mounting plate 102. A proximal end 106 of the spindle 104 is mounted to the mounting plate 102, and the spindle 104 extends along a longitudinal axis 108 to a distal end 107 of the spindle 104. The mounting plate 102 may be mounted to a structural plate 110, which may be provided as part of a building structure. In the example shown, three extension arms 112 are respectively mounted to the spindle 104 for rotational movement about the spindle via hubs 114 at the proximal ends the extension arms. The extension arms 112 each include at their distal end 116 (distal the hub 114 and spindle 104) a knuckle joint assembly 118. The extension arms 112 may include respective housings 115 through which one or more cables may be routed. Load balancing arms 120, which are also referred to as counterbalancing arms, are respectively mounted to the extension arms via the knuckle joint assembly 118. The knuckle joint assembly 118 may rotatably support a spindle 122 of a respective load balancing arm 120 at a proximal end 124 of the load balancing arm 120. The distal end 126 of each load balancing arm 120 is configured with a suitable support hub to support a medical device 128. The medical device 128 may include a surgical light as shown, or a supply console, a patient monitor, a camera detector head, a medical instrument, a ventilator system, a suction device, among others. While the example shown in FIG. 1 includes three extension arms 112 and load balancing arms 120, it will be appreciated that in other embodiments, the medical device suspension system may include fewer (e.g., 1, 2) or more (e.g., 4, 5, etc.) extension arms than are shown.

Figure 2:
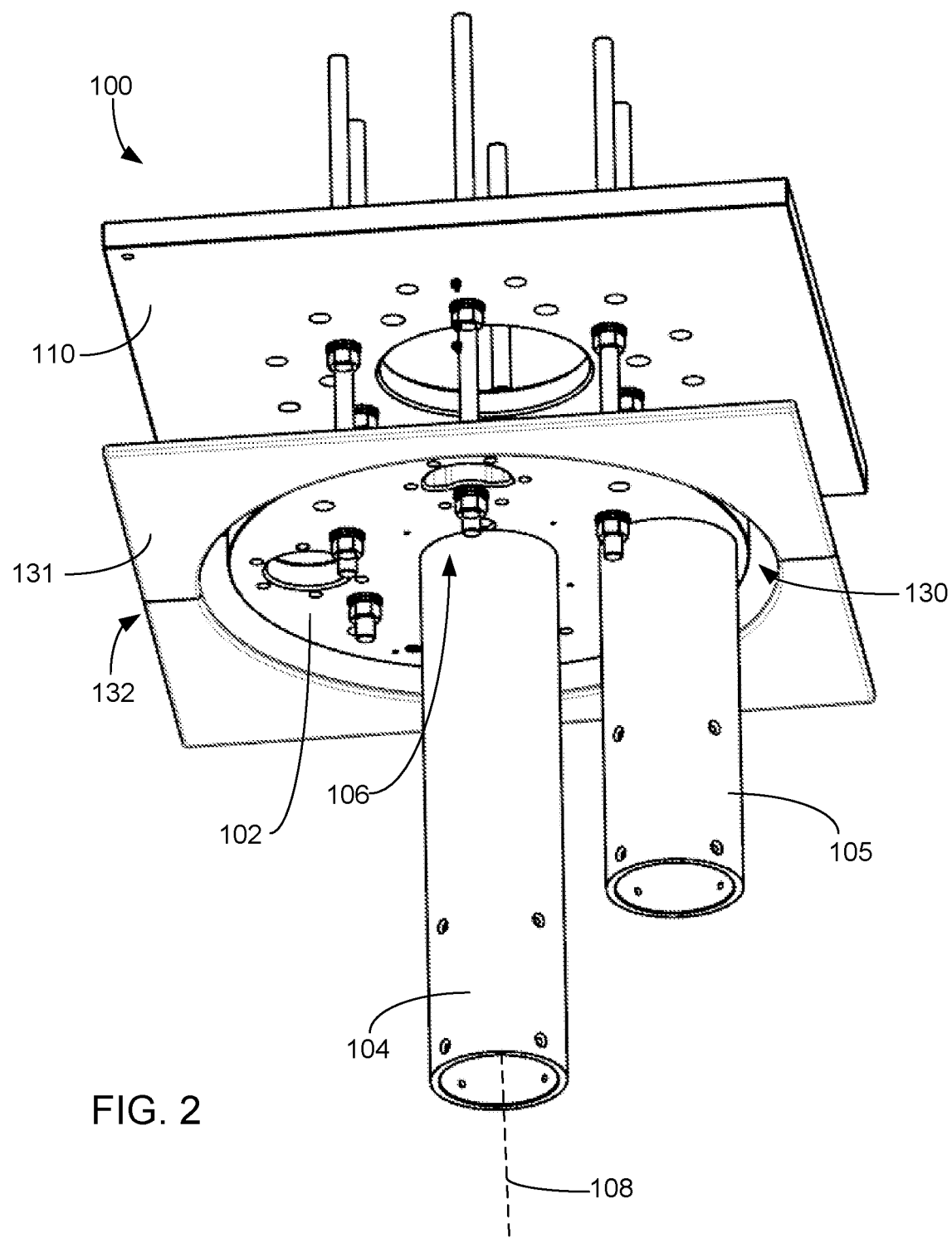
FIG. 2 is a schematic perspective view of parts of an exemplary medical device suspension system in accordance with an embodiment of the present disclosure.

It will also be appreciated that while the exemplary the medical device suspension system is not shown in FIG. 1 as including auxiliary spindles (i.e., the exemplary medical device suspension system in FIG. 1 only includes a primary spindle), in other embodiments the medical device suspension system may include one or more auxiliary spindles. FIG. 2 shows an exemplary embodiment in which one auxiliary spindle 105 is provided in addition to the primary spindle 104 mounted to the mounting plate 102. In other embodiments, the medical device suspension system may include more than one auxiliary spindle (e.g., two, three, four) mounted to the mounting plate 102.

With specific reference to FIG. 2, parts of the medical device suspension system may extend through an opening 130 of a structure 132 into the room in which the device is mounted. In the exemplary embodiment shown, the medical device suspension system is mounted to a structural plate and passes through an opening 130 in a ceiling structure 132 (e.g., a ceiling tile or panel). In other exemplary embodiments, the medical device suspension system is mounted to a structural plate and passes through an opening in a wall structure.

Figure 3:
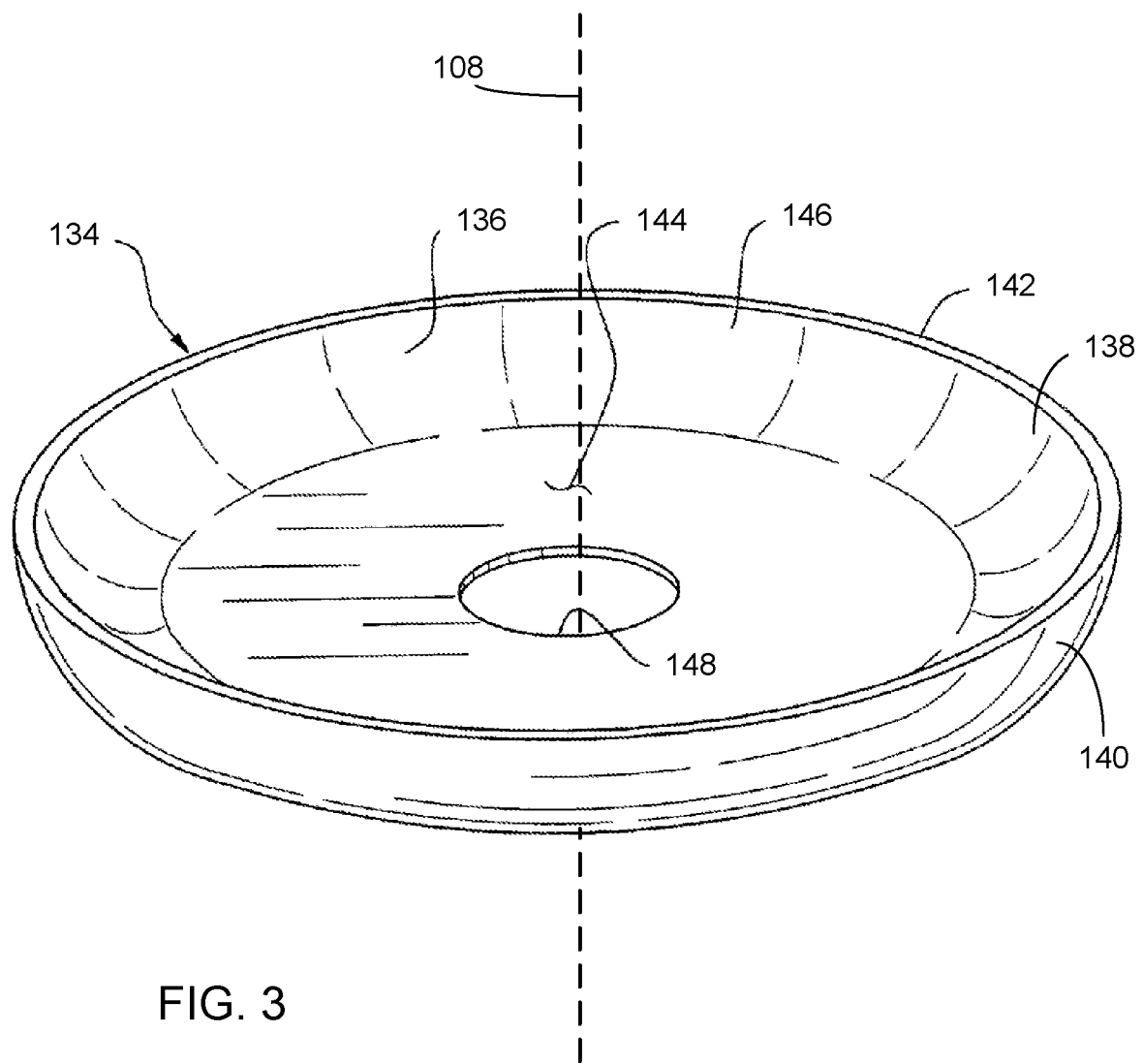
FIG. 3 is a schematic perspective view of an exemplary canopy.
Figure 4:
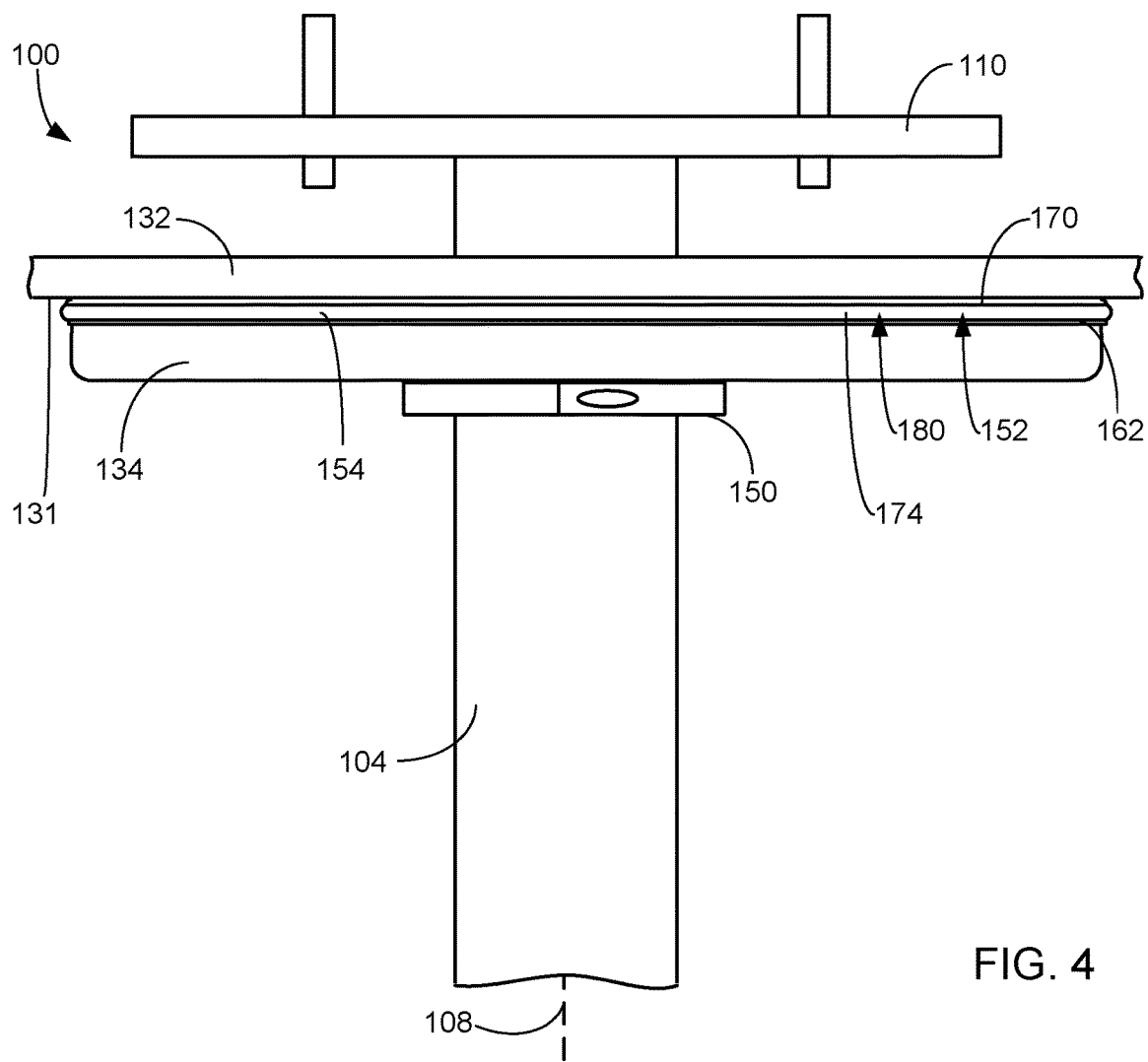
FIG. 4 is a schematic side view of parts of an exemplary medical device suspension system in accordance with an embodiment of the present disclosure.

With additional reference to FIGS. 3 and 4, the medical device suspension system includes a canopy assembly 134. The canopy assembly 134 includes a main body 136 that when engaged with the ceiling or wall structure provides a cosmetic and/or functional cover. The canopy 134 includes opposed major surfaces 138, 140 that are spaced apart from one another in a thickness direction. The canopy also includes an end surface 142 that may face the ceiling or wall structure when the canopy is mounted to the medical device suspension system. The end surface 140 extends between the major surfaces 138, 140 of the canopy. In the exemplary embodiment shown, the canopy is a bowl-shaped configuration and the end surface is annular in shape as viewed in a direction along the longitudinal axis 108. The major surfaces include a planar portion 144 and a curved portion 146. In other embodiments, the canopy may have another suitable shape, e.g., a drum shape, a dome shape, a hemispherical shape, a box shape, or any other suitable shape. In such embodiments, the major surfaces may be constituted by a combination of one or more bottom surfaces and/or side surfaces, depending on the specific shape of the canopy. These other suitable canopy shapes may also include one or more end surfaces that may face the ceiling or wall structure 132 when the canopy is mounted to the medical device suspension system.

The exemplary canopy shown in FIG. 3 includes an orifice 148. When mounted to the medical device suspension system, the primary spindle 104 passes through the orifice 148. In other embodiments where the medical device suspension system includes one or more auxiliary spindles, the canopy may include a suitable number of auxiliary orifices (not shown) and when the canopy is mounted to the medical device suspension system, the auxiliary spindle(s) may respectively pass through the auxiliary orifice(s).

With additional reference to FIG. 4, the canopy may be retained by a securement ring 150 that is attached to the primary spindle 104 (or in some embodiments as described below, the securement ring 150 may be attached to the cable management cover). As shown in FIG. 4, in some embodiments, the securement ring 150 is a clamp ring. The clamp ring is seated below the canopy 134 adjacent the orifice 148. The clamp ring may be annular in shape, forming an inner aperture having a dimension such that the clamp ring is retained in position on the primary spindle 104 via pressure and frictional forces when clamped to the spindle. The body of the clamp ring extends radially from the spindle such that the clamp ring overlaps a portion of the major surfaces of the canopy in a plane orthogonal to the longitudinal axis 108, thereby retaining the canopy and preventing it from sliding down the spindle away from away from the mounting plate.

The shape of the canopy 134 may provide a space within which one or more components may be housed between the canopy and the mounting plate 102. For example, one or more power supplies, controllers, cables, boards, and the like may be mounted to the mounting plate or spindle, or otherwise provided in and/or routed through the space between the canopy and the mounting plate. Accordingly, in addition to providing aesthetics, the canopy may also protect the components housed within this space.

With reference to FIGS. 4-8, a gasket 152 is provided at the end surface 142 of the canopy 134. The gasket 152 extends along at least a portion of the end surface and may provide a damper and/or or seal against a surface 131 of the ceiling or wall structure 132 (e.g., a ceiling tile, panel, and the like). In addition, the gasket 152 is configured as a lighting assembly. As such, in some embodiments, the gasket 152 may provide low level illumination for purposes such as ambient lighting, endo procedures, task lighting, accent lighting, and the like.

Figure 5:
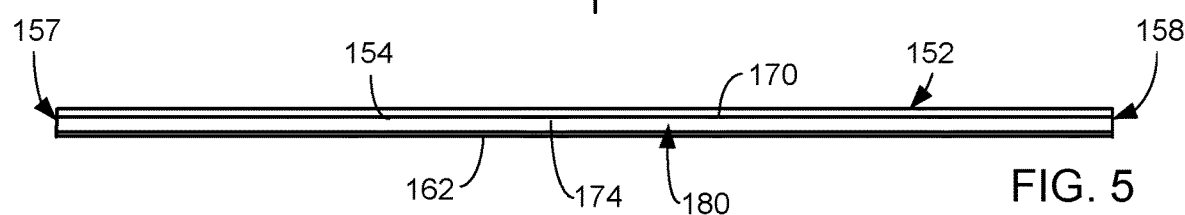
FIG. 5 is a schematic side view of an exemplary gasket in accordance with an embodiment of the present disclosure.
Figure 6A:
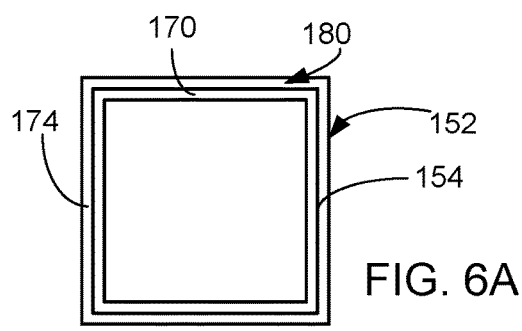
FIGS. 6A and 6B are schematic top views of exemplary gaskets in accordance with embodiments of the present disclosure.
Figure 6B:
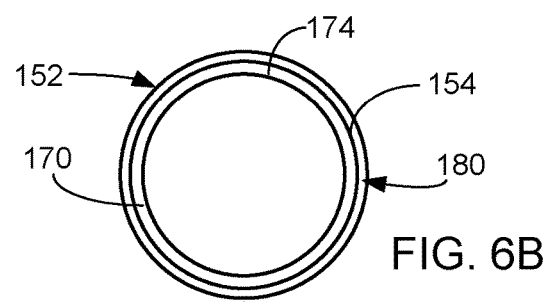

The gasket 152 includes an elongate gasket body 154. In some embodiments, and as exemplified in FIG. 5, the gasket extends in along a length between a first end 157 and a second end 158. The gasket 152 may be provided in a predetermined length or may be cut to length and attached to the canopy 134. In other embodiments, the gasket 152 is formed such that it extends along a perimeter of a predetermined shape and size such that there is no defined first end and second end. FIGS. 6A and 6B are schematic top views showing exemplary formed shapes of the gasket 152. In FIG. 6A, the gasket 152 is formed such that it extends along a perimeter of a square. In FIG. 6B, the gasket 152 is formed such that it extends along a perimeter of a circle. Other exemplary shapes include a rectangle, an octagon, a hexagon, an oval, and the like. The gasket 152 may be flexible so it may be attached to the end surface 142 of the canopy 134 and conform to the shape thereof (e.g., shape of the perimeter as defined by the end surface). Accordingly, even if the gasket 152 is not formed into a predetermined perimeter shape, the gasket 152 can be manipulated such that it conforms to the shape of the component to which it is attaching (e.g., the end surface of the canopy).

The gasket 152 may be formed of a resilient, optically transmissive material. Exemplary materials include materials consisting solely of or including silicone, rubber, polycarbonate, thermoplastic polymer, thermoset polymer, plastic, blends thereof, and the like.

Figure 7:
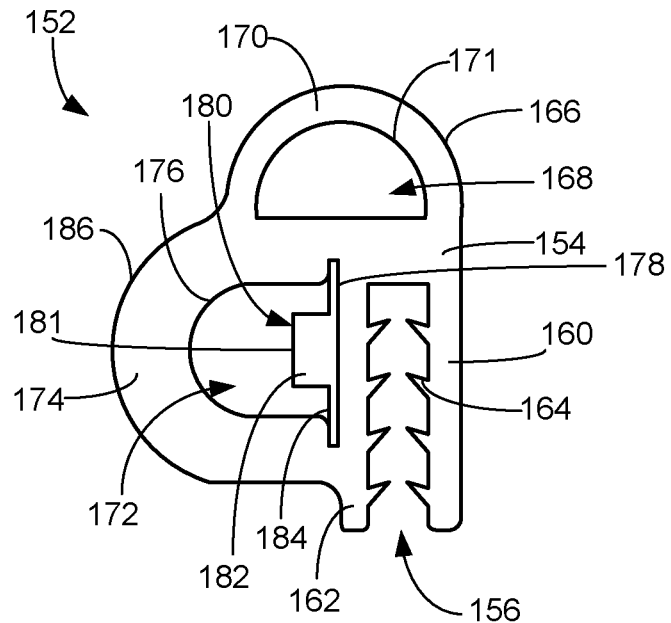
FIG. 7 is a schematic cross-sectional view of an exemplary gasket in accordance with an embodiment of the present disclosure.
Figure 8:
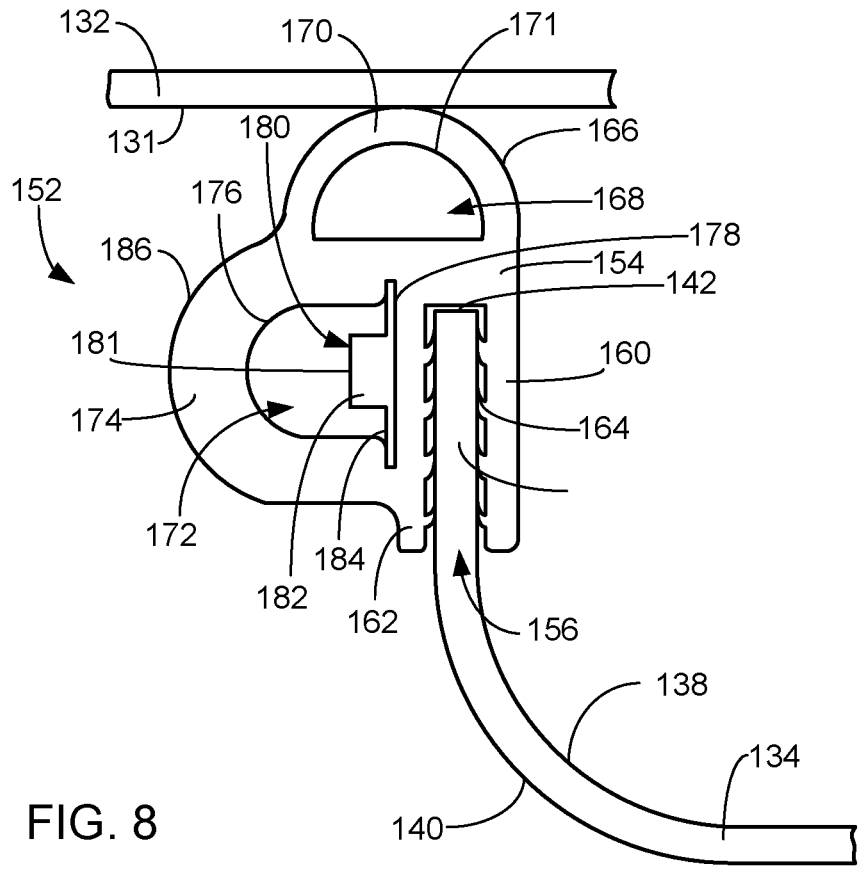
FIG. 8 is a schematic cross-sectional view of parts of an exemplary medical device suspension system in accordance with an embodiment of the present disclosure.

With specific reference to FIGS. 7 and 8, the gasket body 154 includes an attachment channel 156 extending along the length of the gasket. The attachment channel 156 is configured to attach the gasket body 154 to a mount (e.g., a protrusion, flange, wall, or other mounting portion). In the example shown in FIG. 8, the mount is the mounting portion 158 of the canopy 134 proximate the end surface 142 of the canopy. The walls 160, 162 of the channel include protrusions 164 extending from the surfaces thereof that are configured to engage the major surfaces 138, 140 of the canopy 134 proximate the end surface 142 and retain the position of the gasket upon insertion of the portion of the canopy proximate the end surface into the attachment channel. In the example shown, the protrusions 164 are resilient ribs that deflect upon insertion of the canopy into the channel and retain the gasket in position via frictional forces. In other embodiments, the protrusions 164 may have another suitable shape, such as barbs, bumps, and the like. In still other embodiments, the protrusions 164 may be a mix of one or more types of shapes. In still other embodiments, the attachment channel 156 may not include protrusions 164 but the mount may be retained in the attachment channel using an adhesive and/or based on the dimensions of the channel relative to the thickness of the mount. In still other embodiments, the attachment channel 156 may include protrusions 164 and the mount may also be retained in the attachment channel using an adhesive.

The gasket body 154 also includes a sealing protrusion 166 extending along the length of the gasket body 154. The sealing protrusion 166 includes a cavity 168 extending along the length of the gasket. As shown in the cross-sectional view of FIGS. 7 and 8, the cavity 168 is at least partially defined by a contact portion 170 of the gasket body 154. The contact portion 170 is convex in shape and includes an inner wall 171 that at least partially defines the cavity 168. When mounted to the canopy 134, for example, the contact portion 170 may come into contact with the ceiling or wall structure 132 when the canopy is in place (e.g., as shown in FIG. 8). The cavity 168, together with the shape of the contact portion 170 and the resilient property of the gasket material, may allow for the contact portion to deform as a force is applied from the canopy against the ceiling or wall structure 132.

The gasket body 154 further includes a light source cavity 172 extending along the length of the gasket body 154. As shown in the cross-sectional view of FIGS. 7 and 8, the light source cavity 172 is at least partially defined by a light transmission portion 174 of the gasket body 154. The light transmission portion 174 is convex in shape and has an inner wall 176 that at least partially defines the light source cavity 172. An additional inner wall 178 also at least partially defines the light source cavity 172, and may also be referred to as a light source mounting portion 178 of the gasket body 154.

A light source 180 is disposed in the light source cavity 172 and extends along the length of the gasket body 154. The light source 180 is arranged such that light emitted from the light source is incident and transmitted through the light transmission portion 174 of the gasket body 154. The light source cavity 172 is enclosed as viewed in the cross-section shown in FIGS. 7 and 8 (transverse to the length) and in some embodiments is open only at the first and second ends 157, 158. Even in such embodiments, the open ends 157, 158 may be arranged such that they abut one another. As such, closed nature of the light source cavity 172 may provide protection for the light source 180 from liquids or contaminants.

The light source 180 includes one or more solid-state light emitters 182. Exemplary solid-state light emitters 182 include such devices as LEDs, laser diodes, and organic LEDs (OLEDs). In an embodiment where the solid-state light emitters 182 are LEDs, the LEDs may be top-fire LEDs or side-fire LEDs, and may be broad spectrum LEDs (e.g., white light emitters) or LEDs that emit light of a desired color or spectrum (e.g., red light, green light, blue light, or ultraviolet light), or a mixture of broad-spectrum LEDs and LEDs that emit narrow-band light of a desired color. In one embodiment, the solid-state light emitters 182 emit light with no operably-effective intensity at wavelengths greater than 500 nanometers (nm) (i.e., the solid-state light emitters 182 emit light at wavelengths that are predominantly less than 500 nm). In some embodiments, the solid-state light emitters 182 constituting light source 182 all generate light having the same nominal spectrum. In other embodiments, at least some of the solid-state light emitters 182 constituting light source 180 generate light that differs in spectrum from the light generated by the remaining solid-state light emitters 182. For example, two different types of solid-state light emitters 182 may be alternately located along the light source 180.

The light source may include one or more additional components. In the example shown, the solid-state light emitters 182 are mounted to a substrate 184 such as a flexible and/or conformable substrate. In other embodiments, the solid-state light emitters 182 may be mounted to a printed circuit board (PCB). The solid-state light emitters 182 may be arranged linearly or in another suitable pattern along the length of the gasket. The light source 180 may additionally include circuitry, power supply, electronics for controlling and driving the solid-state light emitters 182, and/or any other appropriate components. In some embodiments, one or more of these additional components may be provided in the gasket (e.g., in the light source cavity 172 or otherwise integrated in the gasket). In other embodiments, one or more of these additional components may be provided in the space provided between the mounted canopy and the mounting plate, and may be connected to the solid-state light emitters 182.

In some embodiments, the light source (e.g., the solid-state light emitters 182 mounted to the substrate) may be inserted into the light source cavity after formation of the gasket through one of the open ends of the gasket body. In other embodiments, the light source (e.g., the solid-state light emitters 182 mounted to the substrate) may be provided in the light source cavity during formation of the gasket (e.g., in a co-extrusion, injection molding, or over molding process). The closed nature and geometry may result in adhesive not being required to mount the light source in the light source cavity 172. Although, in some embodiments, adhesive tape (e.g., UV activated adhesive) may be utilized to maintain the light source in the cavity. The light source including a UV activatable adhesive on the substrate may be inserted into the light source cavity from one of the ends 157, 158 of the gasket, and UV light may be applied to activate the adhesive.

The light source cavity 172 is configured such that there is a predetermined distance or gap between the light-emitting surface 181 of the solid-state light emitter 182 and the inner wall 176 of the light transmission portion 174. This distance or gap may serve as light mixing region where light emitted from the solid-state light emitters 182 may spread and mix prior to entering the light transmission portion 174 of the gasket body 154. This distance or gap may help to reduce an unwanted visual effect of LED "hot spots" where LED light sources in the gasket are seen as bright point sources. The reduction in hot spots provides a more uniform appearance of the intensity of the light emitted from the gasket. The distance from the light emitting surface 181 of the light source to the inner wall 176 of the light transmission portion may be defined as the distance along a direction orthogonal to the light emitting surface 181. In some embodiments, the distance from the light emitting surface of the light source to the inner wall 176 of the light transmission portion along a direction orthogonal to the light emitting surface is 0.1 mm to 20 mm. In other embodiments, the distance from the light emitting surface of the light source to the inner wall 176 of the light transmission portion along a direction orthogonal to the light emitting surface is 1 mm to 20 mm. In other embodiments, the distance from the light emitting surface of the light source to the inner wall 176 of the light transmission portion along a direction orthogonal to the light emitting surface is 5 mm to 15 mm. In other embodiments, the distance from the light emitting surface of the light source to the inner wall 176 of the light transmission portion along a direction orthogonal to the light emitting surface is 5 mm to 10 mm. Although, in still other embodiments, the light emitting surface may be arranged such that it is adjacent and in contact with the inner wall 176 of the light transmission portion.

In some embodiments, the gasket material may be specularly transmissive in that it does not provide an optical modifying characteristic to the light passing therethrough (other than refraction that may occur). In other embodiments, the gasket material may modify the light output distribution of the light emitted from the solid-state light emitters 182 and passed through the light transmission portion 176. In some embodiments, the gasket material is diffusive such that light emitted from the solid-state light emitters 182 and passed through the light transmission portion 176 is output from the light transmission portion in a diffuse manner. In some embodiments, the gasket material includes light scattering elements dispersed therein such that light emitted from the LEDs and passed through the light transmission portion is incident a light scattering element and reflected and/or refracted and output from the light transmission portion in a diffuse manner. Diffusion of the light passing through the light transmission portion 176 may help to reduce the unwanted visual effect of LED hot spots and provide a more uniform appearance of the intensity of the light emitted from the gasket.

The light transmission portion 174 has a predetermined thickness (i.e., distance) between the inner wall 176 and the outer surface 186 of the light transmission portion (along a direction orthogonal to the light emitting surface). In some embodiments, the thickness of the light transmission portion is 1 mm to 10 mm. In other embodiments, the thickness of the light transmission portion is 3 mm to 10 mm. In other embodiments, the thickness of the light transmission portion is 5 mm to 10 mm. The thickness of the light transmission portion 174 may help to reduce an unwanted visual effect of LED "hot spots".

Figure 9:
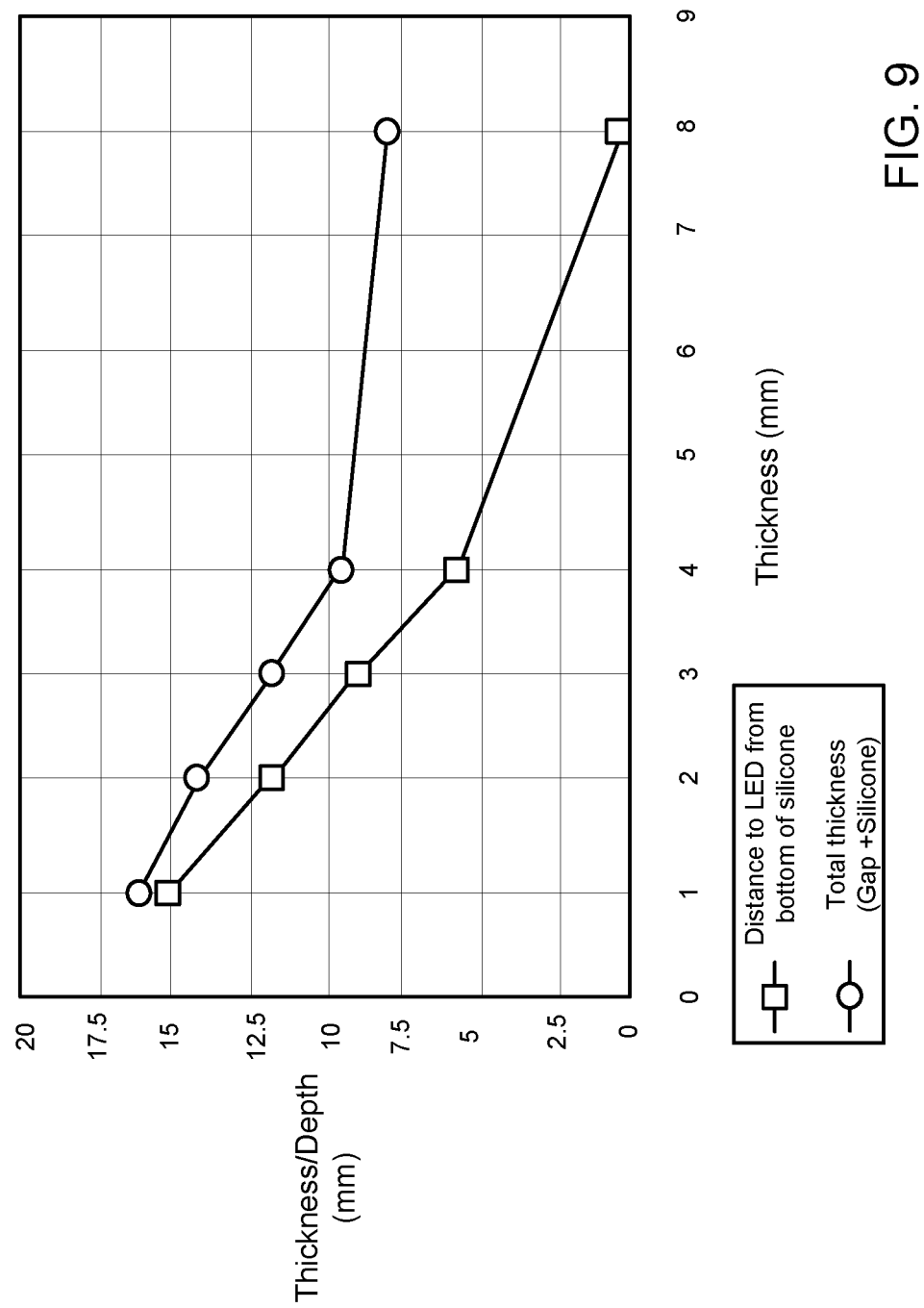
FIG. 9 is a chart showing gasket material thickness and gap distance relative to the presence of LED hot spots.

The thickness of the light transmission portion 174 and the distance from the light emitting surface 181 of the LED to the inner wall of the light transmission portion along a direction orthogonal to the light emitting surface 181 may be set in order to achieve a desired reduction/elimination of the hot spot visual appearance. With reference to FIG. 9, these parameters were tested to determine the effectiveness of the elimination of hot spots. The gasket material used in the test was silicone having a diffusive optical property. Light emitted from the light source was incident the inner wall 176 and passed through the light transmission portion 174, with the light passing through the light transmission portion 174 being diffused as a result of the optical property of the silicone material. As shown in FIG. 9, as the thickness of the light transmission portion is increased, the minimum depth required to eliminate the presence of hot spots decreases. It is also shown that as the thickness of the light transmission portion is increased, the overall thickness (i.e., the distance from the light emitting surface of the LED to the inner surface of the light transmission portion along a direction orthogonal to the light emitting surface together with the thickness of the light transmission portion) is decreased.

The gasket of the present disclosure provides a single component that integrates lighting components and sealing functionality within a small, cost-effective design. The design provides a minimum profile, and may eliminate the need to provide additional components for low level illumination. The gasket design is flexible and allows installation as a single piece without having to be split for maintenance. This may allow the design to have no interruption of the light output. The gasket may provide a seal between the component (e.g., canopy) to which it is attached and the abutted surface (e.g., ceiling) to control transfer of undesired contamination into or out of the room. The gasket provides a lighting solution that does not require interruption of the light source as a compromise to maintainability.

While the gasket has been shown and described primarily in the context of a seal for use in connection with the canopy of a medical device suspension system, it will be appreciated that the gasket may be used in other applications such as table lighting, EMS lighting, cabinet lighting, task lighting, ambient lighting, accent lighting, etc. It will further be appreciated that the design of the gasket may be modified in accordance with the particular application thereof.

Figure 10:
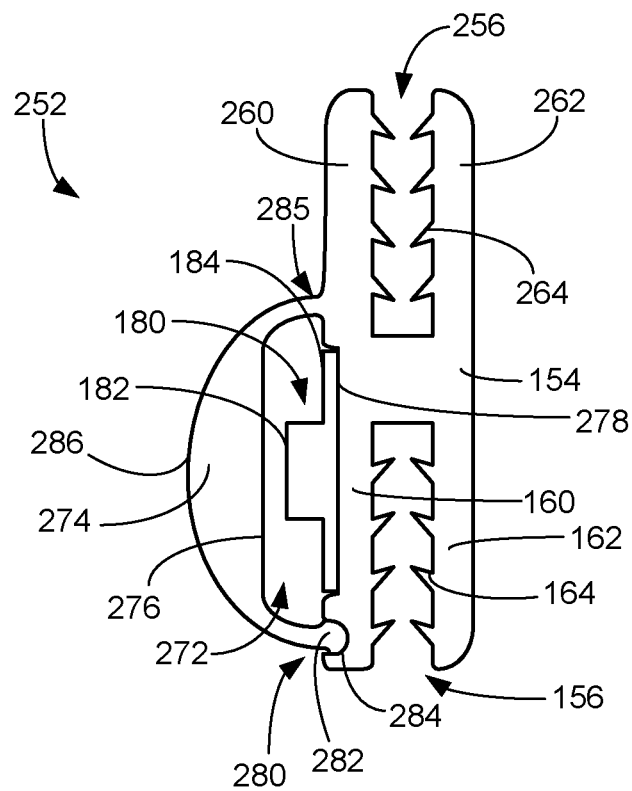
FIG. 10 is a schematic cross-sectional view of an exemplary gasket in accordance with an embodiment of the present disclosure.
Figure 11:
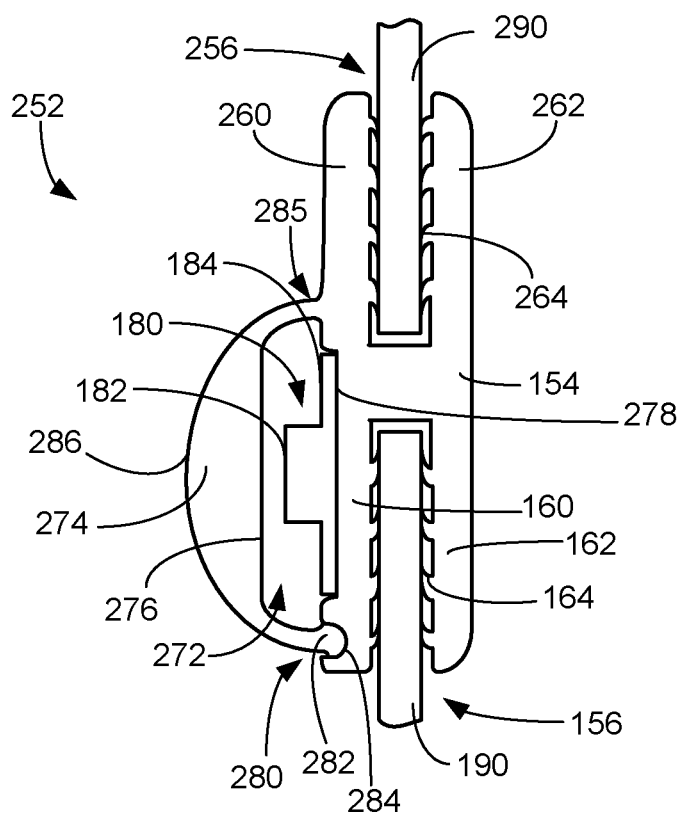
FIG. 11 is a schematic cross-sectional view of parts of an exemplary medical device suspension system in accordance with an embodiment of the present disclosure.

For example, FIGS. 10 and 11 show another exemplary embodiment of a gasket 252 including alternative structural features. Similar to the gasket 152, the gasket 252 includes an elongate gasket body 154. In some embodiments, the gasket extends along a length between a first end and a second end (e.g., as shown in FIG. 5). In other embodiments, the gasket is formed as a predetermined shape (e.g., formed such that it extends along a perimeter of a circle or square like as shown in FIG. 6A or 6B, or in another exemplary shape such as a rectangle, an octagon, a hexagon, an oval, and the like).

The gasket may be formed of a resilient, optically transmissive material. Exemplary materials include materials consisting solely of or including silicone, rubber, polycarbonate, thermoplastic polymer, thermoset polymer, plastic, blends thereof, and the like.

The gasket body 154 includes an attachment channel 156 extending along the length of the gasket. The attachment channel 156 is configured to attach the gasket body 154 to a mount (e.g., a protrusion, flange, wall, or other mounting portion). The walls 160, 162 of the channel include protrusions 164 that are configured to engage the mount (e.g., the major surfaces 138, 140 of the canopy 134 proximate the end surface 142) and retain the position of the gasket upon insertion of the mount into the attachment channel. In the example shown, the protrusions 164 are resilient ribs that deflect upon insertion of the mount into the channel and retain the gasket in position via frictional forces. In other embodiments, the protrusions 164 may have another suitable shape, such as barbs, bumps, and the like. In still other embodiments, the protrusions 164 may be a mix of one or more types of shapes. In still other embodiments, the attachment channel 156 may not include protrusions 164 but the mount may be retained in the attachment channel using an adhesive and/or based on the dimensions of the channel relative to the thickness of the mount. In still other embodiments, the attachment channel 156 may include protrusions 164 and the mount may also be retained in the attachment channel using an adhesive.

The gasket body 154 includes an additional attachment channel 256 extending along the length of the gasket. The additional attachment channel 256 is configured to attach the gasket body 154 to a mount (e.g., a protrusion, flange, wall, or other mounting portion). The mount attached to the additional attachment channel 256 is different from the mount attached to the attachment channel 156. The walls 260, 262 of the channel include protrusions 264 that are configured to engage the mount and retain the position of the gasket upon insertion of the mount into the additional attachment channel. In the example shown, the protrusions 264 are resilient ribs that deflect upon insertion of the mount into the channel and retain the gasket in position via frictional forces. In other embodiments, the protrusions 264 may have another suitable shape, such as barbs, bumps, and the like. In still other embodiments, the protrusions 264 may be a mix of one or more types of shapes. In still other embodiments, the additional attachment channel 256 may not include protrusions 264 but the mount may be retained in the attachment channel using an adhesive and/or based on the dimensions of the channel relative to the thickness of the mount. In still other embodiments, the additional attachment channel 256 may include protrusions 264 and the mount may also be retained in the attachment channel using an adhesive.

In some embodiments, the gasket 252 may be provided at the end surface 142 of the canopy 134 and may extend along at least a portion of the end surface and provide a damper and/or or seal against a surface 131 of the ceiling or wall structure 132 (e.g., a ceiling tile, panel, and the like). As an example, the end surface of the canopy may be retained in the attachment channel 156, and a separate mount associated with the surface of the ceiling or wall structure may be retained in the additional attachment channel 256. In other embodiments, as exemplified in FIG. 11, the gasket 252 may function to retain two parts 190, 290 of a component of the medical device suspension system (e.g., two parts of the canopy, two parts of a cable management cover, etc.), or two different parts of the medical device suspension system. The gasket 252 may join the parts together.

The gasket body 154 further includes a light source cavity 272 extending along the length of the gasket body 154. As shown in the cross-sectional view of FIGS. 10 and 11, the light source cavity 272 is at least partially defined by a light transmission portion 274 of the gasket body 154. The light transmission portion 274 is convex in shape and has an inner wall 276 that at least partially defines the light source cavity 172. An additional inner wall 278 also at least partially defines the light source cavity 172, and may also be referred to as a light source mounting portion 278 of the gasket body 154.

A light source 180 is disposed in the light source cavity 272 and extends along the length of the gasket body 154. The light source 180 is arranged such that light emitted from the light source is incident and transmitted through the light transmission portion 274 of the gasket body 154. Details of the light source are discussed above in connection with the exemplary embodiment shown in FIGS. 7 and 8, and will not be repeated for the sake of brevity.

With reference to the cross-sectional view of FIGS. 10 and 11, the light source cavity 272 is shown as an enclosed cavity. However, the light source cavity 272 differs from light source cavity 172 in that the light source cavity 272 is openable. One of the ends 280 of the light transmission portion 274 is removably connected to a surface of the gasket body. In the exemplary embodiment shown, the end 280 of the light transmission portion 274 is a bulbous end portion 282 that is inserted into and retained in an indentation 284 in the gasket body 154. Because the material of the gasket body is resilient, the other end 285 of the light transmission portion that is integrated with and therefore fixedly attached to the remainder of the gasket body 154 acts as a hinge by which the light transmission portion may move (may be rotated away from the light source 180 upon separation of the removable end 280 from the gasket body). Accordingly, the light transmission portion 274 is separable from the mounting portion at one end 280, which may expose and provide access to the light source 180. The light source as installed in the light source cavity may be accessed by disconnecting the removable end 280 of the light transmission portion 274 from the gasket body 154 and opening the light source cavity via the hinged end 285 of the light transmission portion.

In some embodiments, the light source 180 may be inserted into the light source cavity after formation of the gasket through one of the open ends of the gasket body. In some embodiments, the closed nature and geometry may result in adhesive not being required to mount the light source. Although, in some embodiments, adhesive (e.g., UV activated adhesive, pressure sensitive adhesive) may be utilized to maintain the light source in the cavity.

It will be appreciated that while the embodiment of the gasket 252 shown in FIGS. 10 and 11 include an openable light source cavity, in some embodiments, the gasket 252 may be provided with a light source cavity that is not openable (e.g., similar to that described in connection with the embodiment of the gasket 152 shown in FIGS. 7 and 8). Similarly, while the embodiment of the gasket 152 shown in FIGS. 7 and 8 include a non-openable light source cavity, in some embodiments, the gasket 152 may be provided with an openable light source cavity (e.g., similar to that described in connection with the embodiment of the gasket 252 shown in FIGS. 10 and 11).

The light source cavity 272 is configured such that there is a predetermined distance or gap between the light-emitting surface of the solid-state light emitter 182 and the inner wall 276 of the light transmission portion 274. This distance or gap may serve as light mixing region where light emitted from the solid-state light emitters 182 may spread and mix prior to entering the light transmission portion 274 of the gasket body 154. This distance or gap may help to reduce an unwanted visual effect of LED hot spots where LED light sources in the gasket are seen as bright point sources. The reduction in hot spots provides a more uniform appearance of the intensity of the light emitted from the gasket. The distance from the light emitting surface of the light source to the inner wall 276 of the light transmission portion may be defined as the distance along a direction orthogonal to the light emitting surface. In some embodiments, the distance from the light emitting surface of the light source to the inner wall 276 of the light transmission portion along a direction orthogonal to the light emitting surface is 0.1 mm to 20 mm. In other embodiments, the distance from the light emitting surface of the light source to the inner wall 276 of the light transmission portion along a direction orthogonal to the light emitting surface is 1 mm to 20 mm. In other embodiments, the distance from the light emitting surface of the light source to the inner wall 276 of the light transmission portion along a direction orthogonal to the light emitting surface is 5 mm to 15 mm. In other embodiments, the distance from the light emitting surface of the light source to the inner wall 276 of the light transmission portion along a direction orthogonal to the light emitting surface is 5 mm to 10 mm. Although, in still other embodiments, the light emitting surface may be arranged such that it is adjacent and in contact with the inner wall 276 of the light transmission portion.

In some embodiments, the gasket material may be specularly transmissive in that it does not provide an optical modifying characteristic to the light passing therethrough (other than refraction that may occur). In other embodiments, the gasket material may modify the light output distribution of the light emitted from the solid-state light emitters 182 and passed through the light transmission portion 274. In some embodiments, the gasket material is diffusive such that light emitted from the solid-state light emitters 182 and passed through the light transmission portion 174 is output from the light transmission portion in a diffuse manner. In some embodiments, the gasket material includes light scattering elements dispersed therein such that light emitted from the LEDs and passed through the light transmission portion is incident a light scattering element and reflected and/or refracted and output from the light transmission portion in a diffuse manner. Diffusion of the light passing through the light transmission portion 274 may help to reduce the unwanted visual effect of LED hot spots and provide a more uniform appearance of the intensity of the light emitted from the gasket.

The light transmission portion 274 has a predetermined thickness (i.e., distance between the inner wall 276 and the outer surface 286 of the light transmission portion. In some embodiments, the thickness of the light transmission portion is 1 mm to 10 mm. In other embodiments, the thickness of the light transmission portion is 3 mm to 10 mm. In other embodiments, the thickness of the light transmission portion is 5 mm to 10 mm. The thickness of the light transmission portion 174 may help to reduce an unwanted visual effect of LED "hot spots"

The thickness of the light transmission portion and the distance from the light emitting surface of the LED to the inner wall of the light transmission portion along a direction orthogonal to the light emitting surface may be set in order to achieve a desired reduction/elimination of the hot spot visual appearance. Reference to FIG. 9 (described above), which shows the effectiveness of these parameters in the elimination of hot spots.

Figure 12:
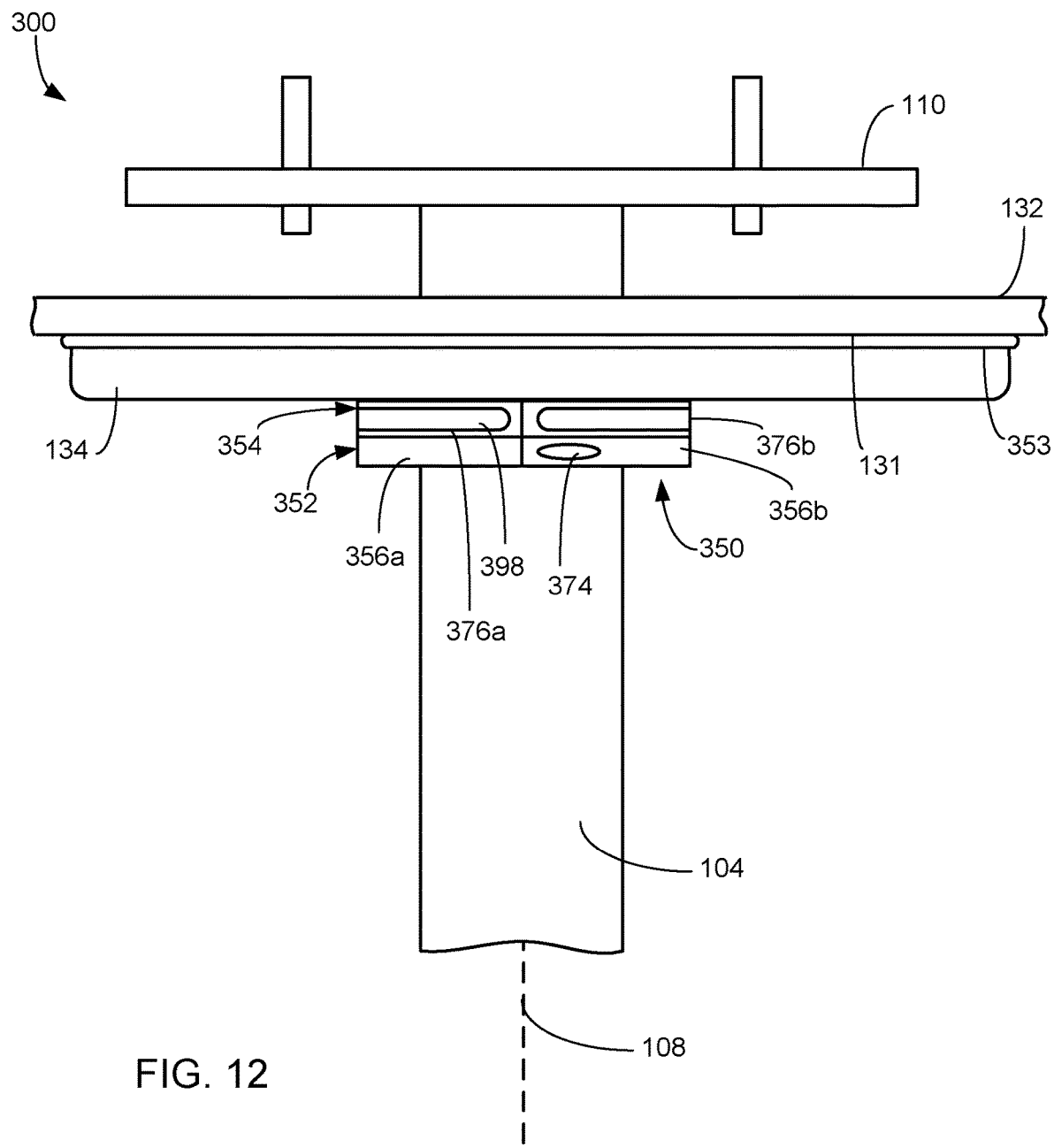
FIG. 12 is a schematic side view of parts of an exemplary medical device suspension system in accordance with an embodiment of the present disclosure.

Turning now to FIG. 12, another exemplary embodiment of a medical device suspension system including a lighting assembly is shown at 300. The medical device suspension system includes components similar to those described in connection with FIGS. 1-4, including a mounting plate 102, spindle 104, and canopy 134. However, the gasket 353 provided between the canopy and the ceiling does not include a lighting assembly. The gasket 353 may be formed of a resilient material, and may be opaque or optically transmissive. Exemplary gasket materials include materials consisting solely of or including silicone, rubber, polycarbonate, thermoplastic polymer, thermoset polymer, plastic, blends thereof, and the like.

In addition, a securement ring 350 is attached to the primary spindle 104 for retaining the canopy 134. As such, in some embodiments, the securement ring 350 includes a light source that may provide low level illumination for purposes such as ambient lighting, endo procedures, task lighting, accent lighting, and the like. With additional reference to FIG. 13, in some embodiments, the securement ring 350 includes a clamp portion 352 and a lighting assembly portion 354. The securement ring 350 is seated below the canopy 134 adjacent the orifice (e.g., as a result of securing the clamp portion 352 to the spindle via the clamp portion). The securement ring 350 may be secured to the primary spindle 104 or surface to which it is secured (e.g., via pressure and frictional forces when clamped thereto), and may retain the canopy and prevent it from sliding down the spindle (or surface to which it is mounted) away from away from the mounting plate.

The clamp portion 352 of the securement ring 350 includes a first segment 356a and a second segment 356b that collectively form a clamp ring. The formed clamp ring is annular in shape and includes inner surface 360 (formed from the inner surfaces of the clamp portion segments) that forms an inner aperture 362, as well as an outer surface 364 (formed from the outer surfaces of the clamp portion segments) that is displaced radially outwardly from the inner surface 360. The inner aperture 362 may have a dimension such that the clamp ring is retained in position on the primary spindle 104 via pressure and frictional forces when clamped to primary spindle. Each clamp portion segment 356a, 356b is semi-annular in shape and curves about the longitudinal axis 108 between a first end 366 and a second end 368. Each clamp portion segment also has a height along the longitudinal direction and includes a top end 370 and a bottom end 372. The outer surface 364 curves about the longitudinal axis between the first end 366 and the second end 368 and also extends along the longitudinal axis. Similarly, the inner surface 360 curves about the longitudinal axis between the first end 366 and the second end 368 and also extends along the longitudinal axis.

In some embodiments, the first end 366 of one segment 356a of the clamp portion 352 includes a fastening interface that is complimentary to the fastening interface provided at the second end 368 of the other segment 356b of the clamp portion 352. In an example, each segment 356a, 356b of the clamp portion 352 may include a female screw receptacle at its first end 366 and an orifice 374 at its second end 368. When the segment 356a, 356b of the clamp portion 352 are arranged such that the first end 366 of the first segment 356a is adjacent the second end 368 of the second segment 356b, a fastener (e.g., screw) may be used to secure the portions together via the attachment interfaces. Similarly, when the second end 368 of the first segment 356a is adjacent the first end 366 of the second segment 356b, a fastener (e.g., screw) may be used to secure the portions together via the attachment interfaces. In other embodiments (not shown), a hinge may couple one of the ends of one segment 356a of the clamp portion 352 to another end of the other segment 356b. In such embodiments, the segments 356a, 356b may move relative to one another via the hinge (e.g., for purposes of mounting the securement ring 350), and the segments 356a, 356b may be fastened together using the respective attachment interfaces at their unhinged ends.

The lighting assembly portion 354 of the securement ring 350 includes a first segment 376a and a second segment 376b that collectively form a light source ring. The formed light source ring is annular in shape and includes inner surface 378 (formed from the inner surfaces of the clamp portion segments) that forms an inner aperture 380, as well as an outer surface 382 (formed from the outer surfaces of the clamp portion segments) that is displaced radially outwardly from the inner surface 378. Each lighting assembly portion segment 376a, 376b is semi-annular in shape and curves about the longitudinal axis 108 between a first end 384 and a second end 386. Each lighting assembly portion segment also has a height along the longitudinal direction and includes a top end 388 and a bottom end 390. The outer surface 382 curves about the longitudinal axis between the first end 384 and the second end 386 and also extends along the longitudinal axis. Similarly, the inner surface 378 curves about the longitudinal axis between the first end 384 and the second end 386 and also extends along the longitudinal axis.

The segments 376a, 376b of the lighting assembly portion 354 correspond to the segments 356a, 356b of the clamp portion 352 and may in some embodiments be removably attached to the segments of the clamp portion 352. A segment of the lighting assembly portion may be attached to a segment of the clamp portion via pins/holes, slots/grooves, screws, clamps, adhesive, and/or any other suitable fasteners. In the exemplary embodiment shown in FIG. 13, the bottom surface 390 of the segment of the lighting assembly portion includes pins 392 and the top surface 370 of the corresponding segment of the clamp portion includes holes 394 that cooperate with the pins. Upon inserting the pins into the respective holes, frictional forces between the pins and holes may retain the segment of the lighting assembly portion and the corresponding segment of the clamp portion together.

Figure 14:
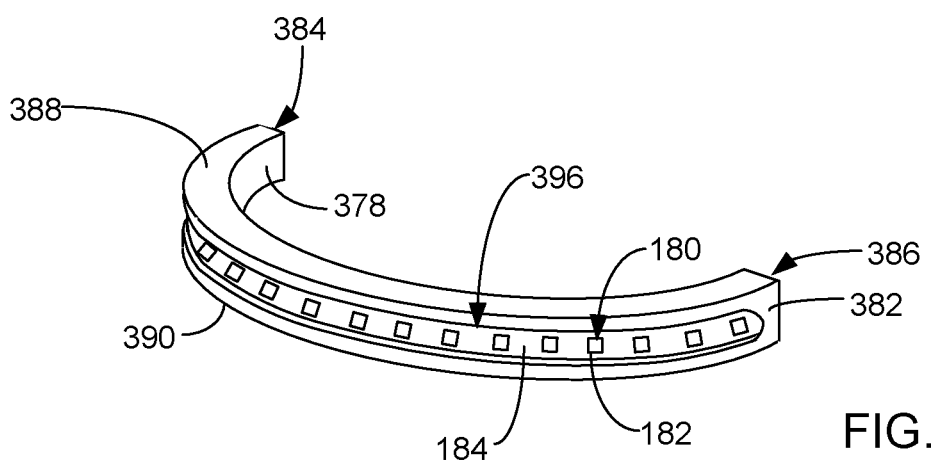
FIG. 14 is a schematic view of parts of an exemplary securement ring.

With additional reference to FIG. 14, each segment of the lighting assembly portion includes a recess 396 at its outer surface. The segment of the lighting assembly portion shown in FIG. 14 is shown without a lens so that the recess can be seen. A light source 180 is disposed in the recess and includes one or more solid-state light emitters 182. The light source 180 may also include one or more additional components. In the example shown, the solid-state light emitters 182 are mounted to a substrate 184. Details of the light source, including the solid-state light emitters and one or more additional components are discussed above in connection with the exemplary embodiment shown in FIGS. 7 and 8, and will not be repeated for the sake of brevity.

In some embodiments, a lens cover 398 covers the recess 396. The lens cover 398 may be any suitable material, including plastic, glass, rubber, silicone, and the like. The light source 180 is arranged such that light emitted from the light source 180 is incident and transmitted through the lens cover 398. In some embodiments, the lens cover 398 provides an optical modifying characteristic to the light transmitted therethrough. For example, the lens cover may modify the light output distribution (e.g., in a diffuse manner) and/or the spectrum of light that is output from the light source 180 and transmitted therethrough. The lens cover may also protect the light source from damage. In other embodiments, no lens cover is provided.

One or more cables 399 may be provided for powering/controlling the light source. In some embodiments, the cables 399 may be routed through the canopy (e.g., through the orifice 148 or through one or more additional orifices provided in the canopy 134).

Figure 13:
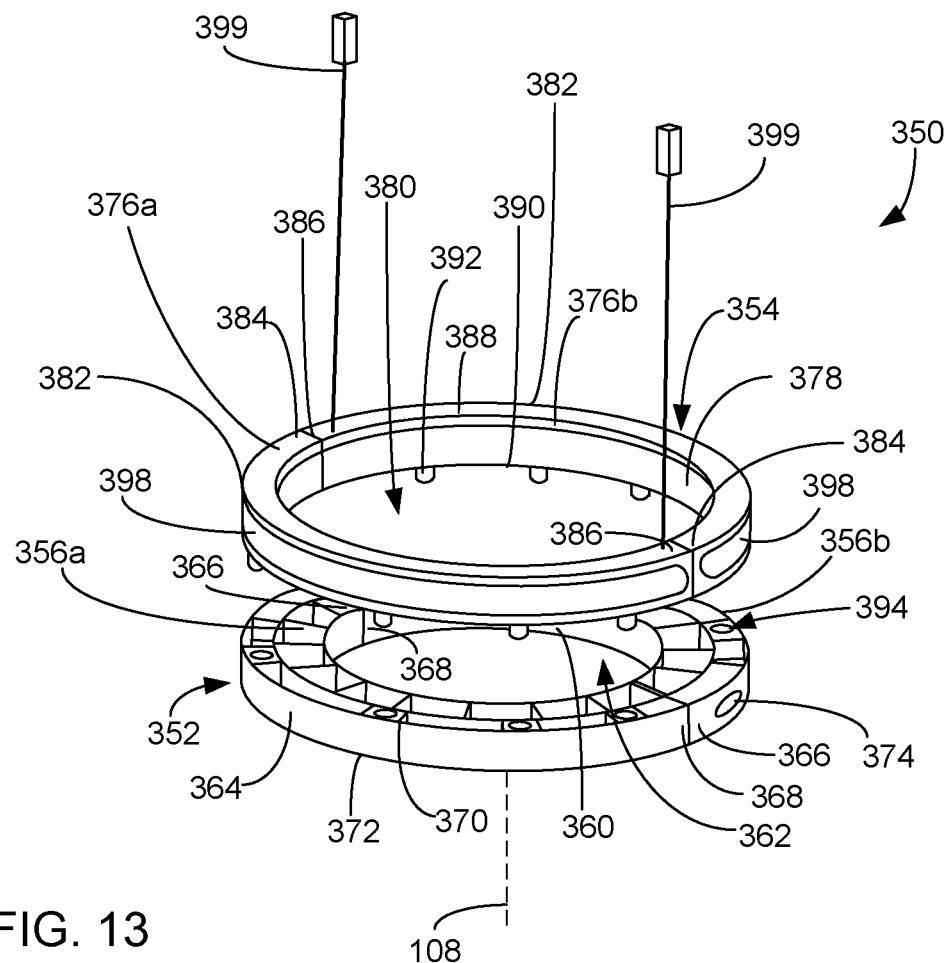
FIG. 13 is a schematic perspective view of an exemplary securement ring.

In embodiment of FIGS. 12 and 13, the diameter of the aperture 362 of the clamp portion 352 is different (e.g., smaller) than the diameter of the aperture formed by the lighting assembly portion 354. As such, only the inner surface of the clamp portion may be in contact with the spindle. The clamp portion (if removable) may be interchanged with other clamp portion of different diameters to accommodate attachment to different sized spindles or other components. Hence, the clamp portion may be swapped out for a clamp portion having a different sized aperture (e.g., one suitable for attachment to a cable management cover 369 placed over the spindle). The interchangeability of the clamp portion is exemplified in FIGS. 15 and 16. In this exemplary embodiment, a cable management cover 369 is provided over the spindle. As such, the clamp portion of the securement ring 350 is attached to the outer major surface of the cable management cover 369 instead of the spindle. As shown in FIG. 13, the clamp portion that may be attached to the lighting assembly portion has a larger inner diameter such that fastening of the segments of the clamp portion together around the cable management cover 369 results in the support right being maintained in position via frictional forces.

While embodiments described above show that the clamp portion may be removably attached to the lighting assembly portion, in other embodiments, the clamp portion may be fixedly attached to the lighting assembly portion. In some embodiments, the clamp portion and the lighting assembly portion are integrally formed. In other embodiments, the clamp portion and the lighting assembly portion are separate pieces that may be permanently attached to one another (e.g., via glue or adhesive).

Figure 15:
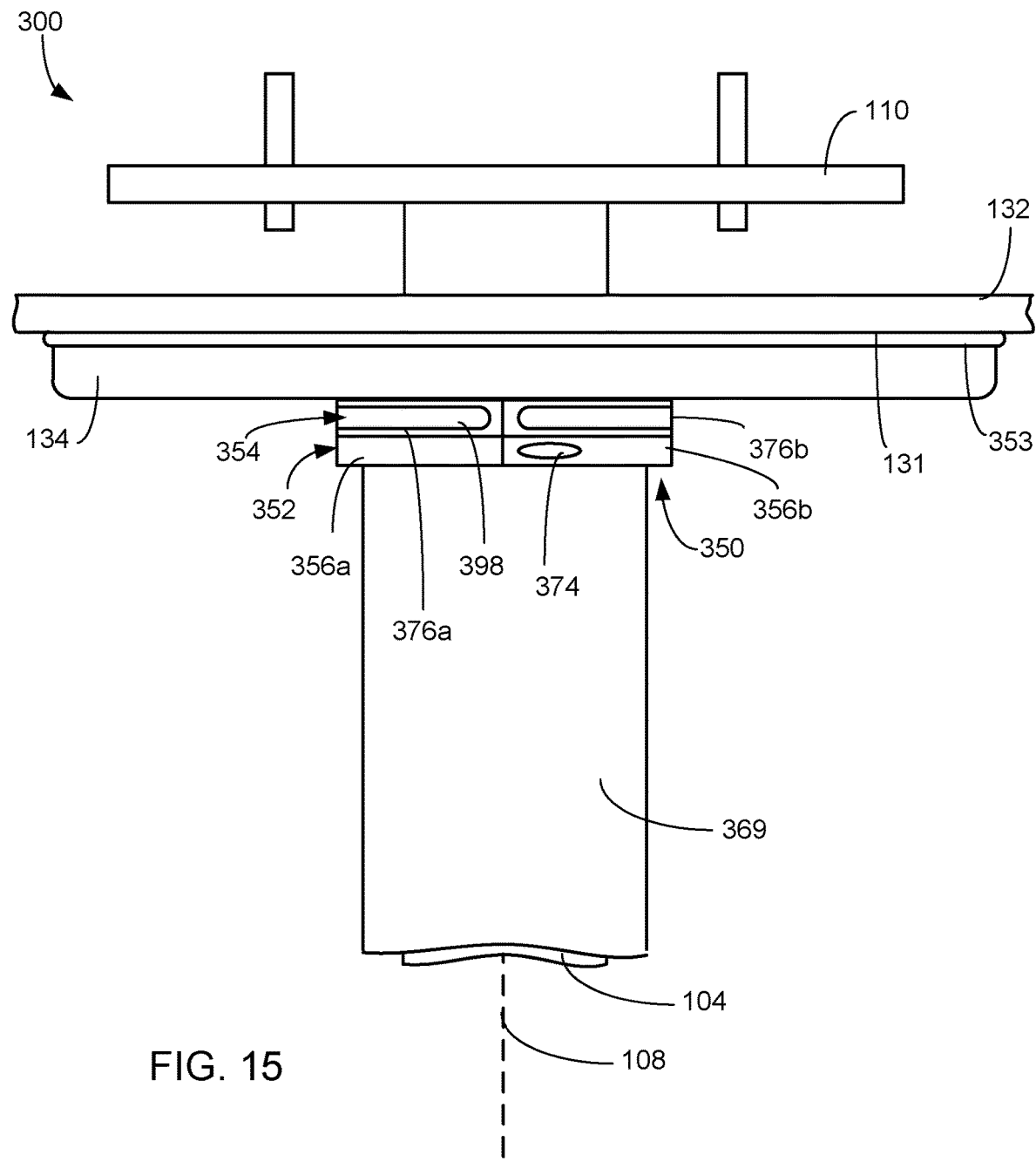
FIG. 15 is a schematic side view of parts of an exemplary medical device suspension system in accordance with an embodiment of the present disclosure.
Figure 16:
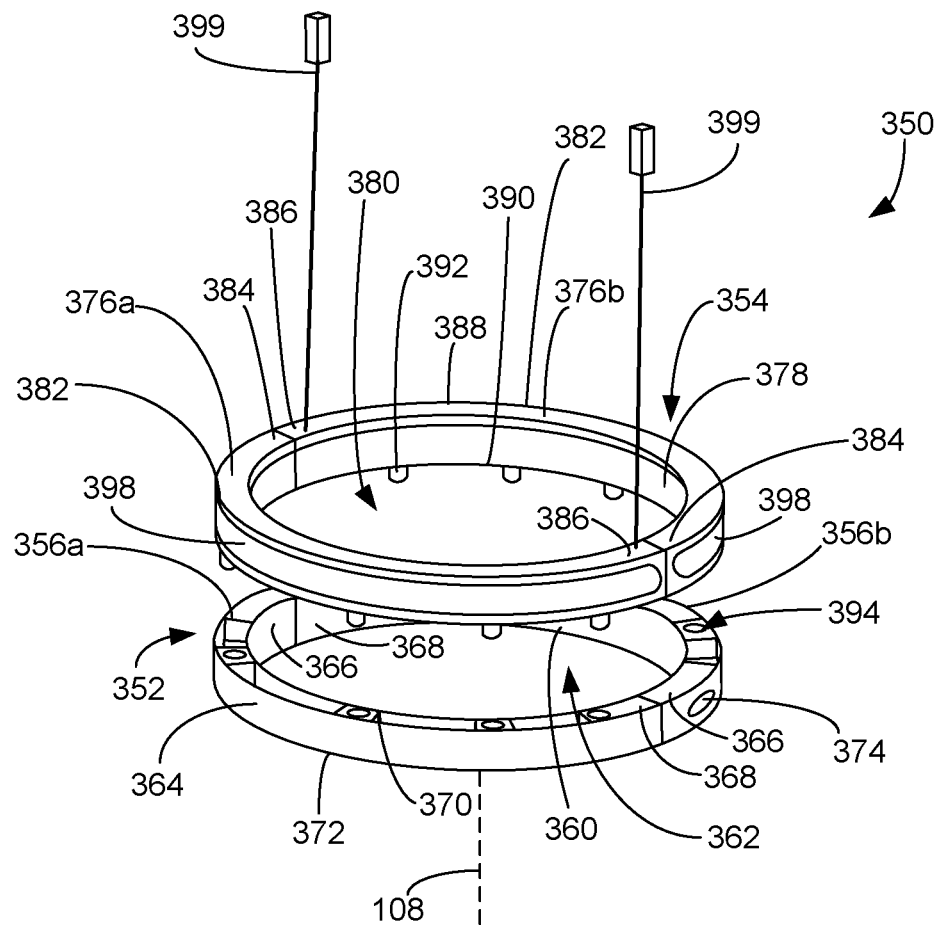
FIG. 16 is a schematic perspective view of an exemplary securement ring.
Figure 17:
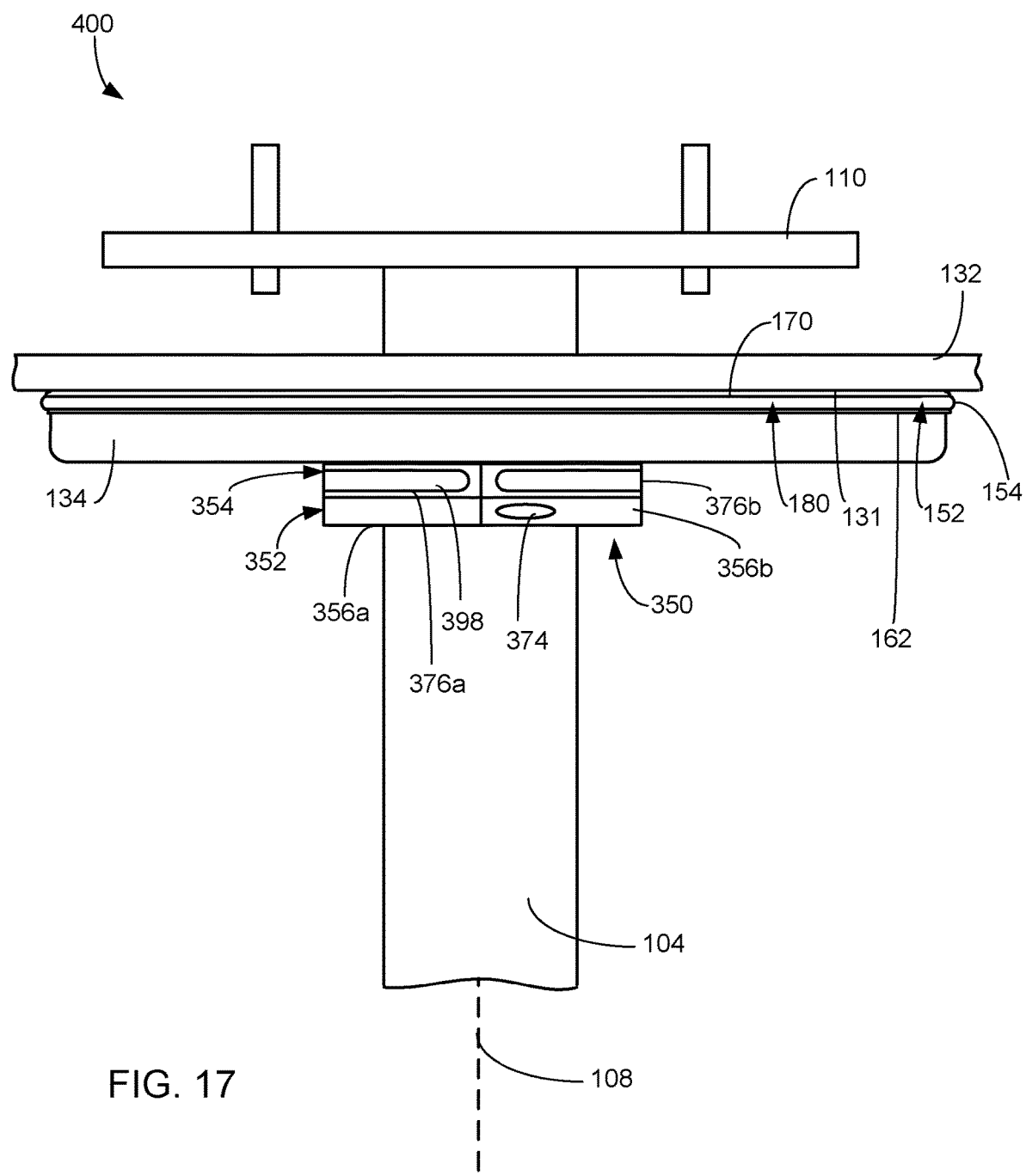
FIG. 17 is a schematic side view of parts of an exemplary medical device suspension system in accordance with an embodiment of the present disclosure.
Figure 18:
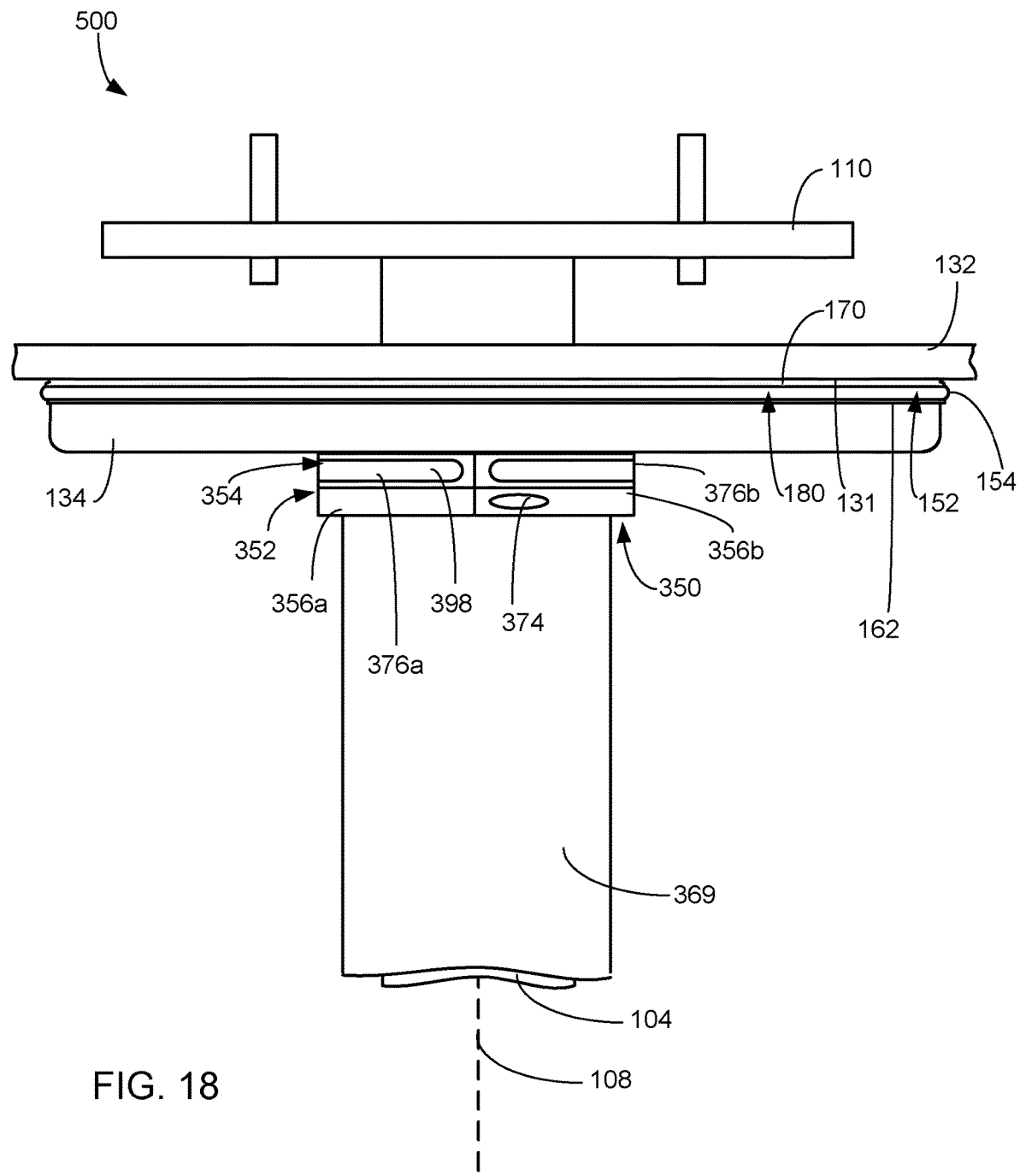
FIG. 18 is a schematic side view of parts of an exemplary medical device suspension system in accordance with an embodiment of the present disclosure.

In the embodiments described above, the medical device suspension system is shown as including one of the gasket including a light source or the securement ring including a light source. As shown in FIGS. 17 and 18, in some embodiments, the medical device suspension system 400, 500 may include both the gasket including a light source and the securement ring including a light source. In both FIGS. 17 and 18, a gasket is included similar to that shown in FIGS. 4-6. In FIG. 17, the securement ring is attached to the spindle and the securement ring is configured similar to that shown in FIGS. 12 and 13 where the clamp portion has an inner diameter corresponding to the outer major surface of the spindle (and is smaller than that of the inner diameter of the lighting assembly portion). In FIG. 15, the securement ring is attached to the cable management cover 369 and the securement ring is configured similar to that shown in FIGS. 15 and 16 where the clamp portion has an inner diameter corresponding to the outer major surface of the cable management cover 369 (and is about the same than that of the inner diameter of the lighting assembly portion).

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device suspension system, comprising:
 a spindle;
 a canopy comprising opposed major surfaces that are spaced apart from one another in a thickness direction, an end surface extending between the opposed major surfaces, and an orifice extending through the opposed major surfaces, the spindle extending through the orifice; and
 a lighting assembly, comprising:
  an elongate gasket body extending along a length and formed of an optically transmissive material, the gasket body comprising:
   a light source cavity extending along the length, the light source cavity at least partially defined by a light transmission portion; and
   an attachment channel extending along the length, the attachment channel configured to attach the gasket body to a mount; and
  a light source disposed in the light source cavity,
 wherein the end surface of the canopy is disposed in the attachment channel.

2. The medical device suspension system of claim 1, wherein the gasket body further comprises a sealing protrusion extending along the length, the sealing protrusion comprising a cavity extending along the length and being at least partially defined by a convex contact portion as viewed in a plane transverse to the length.

3. The medical device suspension system of claim 1, wherein the gasket body further comprises an additional attachment channel extending along the length, the additional attachment channel configured to attach the gasket body to an additional mount.

4. The medical device suspension system of claim 1, wherein the gasket body extends along the length between a first end and a second end, the light source cavity being open at at least one of the first end and the second end.

5. The medical device suspension system of claim 1, wherein the length of the gasket extends along a perimeter of a predetermined shape.

6. The medical device suspension system of claim 1, wherein the material of the gasket body comprises silicone, rubber, polycarbonate, thermoplastic polymer, thermoset polymer, plastic, or a blend of two or more thereof.

7. The medical device suspension system of claim 6, wherein the material diffuses light emitted from the light source and transmitted therethrough.

8. The medical device suspension system of claim 1, wherein the light source comprises one or more solid-state light emitters.

9. The medical device suspension system of claim 8, wherein the one or more solid-state light emitters are mounted on a flexible substrate.

10. The medical device suspension system of claim 1, wherein the attachment channel comprises protrusions configured to engage the mount upon insertion into the attachment channel.

11. The medical device suspension system of claim 10, wherein the protrusions comprise one or more of ribs, barbs, or bumps.

12. The medical device suspension system of claim 1, wherein:
 the light transmission portion comprises an inner surface facing a light emitting surface of the light source; and
 a distance from the light emitting surface of the light source to the inner surface along a direction orthogonal to the light emitting surface is 1 mm to 20 mm.

13. The medical device suspension system of claim 12, wherein the distance from the light emitting surface of the light source to the inner surface along a direction orthogonal to the light emitting surface is 5 mm to 10 mm.

14. The medical device suspension system of claim 1, wherein a thickness of the light transmission portion along a direction orthogonal to the light emitting surface is 1 mm to 10 mm.

15. The medical device suspension system of claim 1, wherein a thickness of the light transmission portion along a direction orthogonal to the light emitting surface is 5 mm to 10 mm.

16. The medical device suspension system of claim 1, wherein the spindle extends through a ceiling or wall structure and the canopy is positioned adjacent a surface of the ceiling or wall structure with the lighting assembly in contact with the surface.

17. The medical device suspension system of claim 1, wherein a securement ring retains the canopy in place with respect to the spindle.

18. The medical device suspension system of claim 17, wherein the securement ring comprises an additional light source.

19. The medical device suspension system of claim 1, wherein the spindle extends along a longitudinal axis, and the lighting assembly is configured to radially emit light about the longitudinal axis.

* * * * *